United States Patent
Hageman et al.

(10) Patent No.: US 6,548,483 B2
(45) Date of Patent: Apr. 15, 2003

(54) NUTRITIONAL PREPARATION COMPRISING RIBOSE AND MEDICAL USE THEREOF

(75) Inventors: Robert Johan Joseph Hageman, Waddinxveen (NL); Rudolf Leonardus Lodewijk Smeets, Waddinxveen (NL); George Verlaan, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 10/178,736

(22) Filed: Jun. 25, 2002

(65) Prior Publication Data

US 2002/0183263 A1 Dec. 5, 2002

Related U.S. Application Data

(62) Division of application No. 09/566,381, filed on May 8, 2000, now Pat. No. 6,420,342.

(51) Int. Cl.[7] .................. A61K 31/70; A61K 31/50; A61K 31/195
(52) U.S. Cl. ............ 514/23; 514/52; 514/249; 514/561; 514/565
(58) Field of Search ............ 514/23, 52, 249, 514/561, 565

(56) References Cited

U.S. PATENT DOCUMENTS

| 4,871,718 A | 10/1989 | Carniglia |
| 5,700,590 A | 12/1997 | Masor et al. |

FOREIGN PATENT DOCUMENTS

| DE | 2231 989 | 7/1973 |
| EP | 0 652 012 A1 | 5/1995 |
| WO | 92/15311 | 9/1992 |
| WO | 99/65476 | 12/1999 |
| WO | 01/28365 A1 | 4/2001 |

*Primary Examiner*—Raymond Henley, III
(74) *Attorney, Agent, or Firm*—Young & Thompson

(57) ABSTRACT

Trauma, surgery, inflammation, subfertility, pregnancy, lactation problems, gut disorders, infant nutrition, cancer, arthritis and other joint problems, vascular problems and cardio-or cerebro-vascular problems, ischaemia, aging, impaired immune function, burns, sepsis, malnutrition, problems with liver, pancreas or kidneys, malaria, cystic fibrosis, migraine, neurological problems, respiratory infections, improvement of sports results, muscle soreness, drug intoxication and pain can be treated with a nutritional composition containing effective amounts of ribose and folic acid, optionally combined with other components such as niacin, histidine, glutamine, orotate, vitamin B6 and other components.

28 Claims, No Drawings

NUTRITIONAL PREPARATION COMPRISING RIBOSE AND MEDICAL USE THEREOF

This is a divisional application of U.S. Ser. No. 09/566,381 filed May 8, 2000, now U.S. Pat. No. 6,420,342.

The invention is related to nutritional, pharmaceutical, or dietetic preparations that comprise ribose or folic acid or functional analogs thereof and the use of these compositions in the prevention or treatment of specific diseases that are related to disorders or insufficient of total nucleotide metabolism.

BACKGROUND OF THE INVENTION

Nucleotides are heterocyclic compounds that occur in all mammals. Nucleotides consist of a purine or pyrimidine base, a sugar unit and one to three phosphate groups. The major purine bases that occur in the human body are adenine (6-aminopurine), guanine (2-amino-6-hydroxypurine), hypoxanthine (6-hydroxypurine) and xanthine (2,6-dihydroxypurine); the major pyrimidines are uracil (2,4-dihydroxypyrimidine), cytosine (2,4-dihydroxy-5-methylpyrimidine) and thymine (4-amino-2-hydroxypyrimidine). The sugar moiety can be ribose (in ribonucleosides) or 2-deoxyribose. The sugar moiety is connected to the base through a β-N-glycosidic bond at N9 of the base; the phosphate groups are connected to the sugar moiety through the 3' or 5' position. When the phosphate groups are split from nucleotides compounds called nucleosides are formed.

For the purpose of this document, total nucleotide metabolism (TNM) is defined as the combination of all biochemical pathways in which nucleotides, their precursors and metabolites are directly involved as main ingredients and that occur in the body of mammals. The pathways include the synthetic routes for purines and pyrimidines, both de novo and salvage pathways, starting from carbamoyl phosphate and 5-phosphoribosyl-1-pyrophosphate (PRPP), respectively. They also include the interconversions of the various nucleotides into each other, the phosphorylation and dephosphorylation reactions of respectively nucleosides and nucleotides and the catabolic pathways of nucleotides to the compounds that are cleared from the body. They do not include the further reactions of phosphoric groups thus split off from the phosphorylated nucleotides.

Nucleotides and their related metabolites play a key role in life, as has been described in the biochemical literature. Triphosphorylated forms, and especially adenosine triphosphate (ATP), are the main forms of chemical energy in mammal's body. This type of energy is for example required to allow desirable biochemical reactions to occur at a substantial rate, to maintain ionic gradients over membranes and to allow transport of some important components over membranes. Nucleotides also can provide phosphate in a lot of biochemical reactions. Nucleotides (bases) can form building blocks for DNA and RNA. Nucleotides and their derivatives can serve as mediators or regulators of many metabolic processes; for example the cyclic form of the monophosphates of adenosine and guanosine function as a second messenger after activation of receptors in the membrane. Due to allosteric effects they regulate many pathways. ADP is involved in platelet aggregation. Adenosine is a potent vasodilator and receptors have been described for other nucleic acid bases as well. Nucleotides are also part of many key cofactors such as NAD, FAD and CoA.

Nucleotides also activate intermediates in many reactions. Interconversion reactions of monosaccharides require activation by means of various nucleotides; these monosaccharides form important constituents of glycoproteins. Ethanolamine also requires activation before it can be modified into choline, and ATP is needed to activate methionine in order to have it function as a methyl donor.

Nucleotides or precursors thereof can be formed in the body or be consumed from the diet. Nucleotides from diet can be broken down in the digestive tract to nucleosides and nucleic acid bases, which can be rapidly absorbed by the gut and can be reassembled to nucleotides and related metabolites. Xanthines occur widely in drinks and chocolate.

Nucleotides can be synthesized de novo in several tissues using a pathway that requires the presence of much energy (ATP) and many reactants. That is why the human body is equipped with salvage systems that allow effective reuse of catabolic products of nucleotides.

Under certain conditions, e.g. when an unbalanced diet was consumed or when (severe) tissue damage has occurred in a short period of time, the body is temporarily exposed to large amounts of nucleic acids. Pyrimidines are in this case catabolized to beta-aminoisobutyric acid (thymine) or beta-alanine (e.g. uracil) that can be cleared through the urine. Beta-alanine can also be used for biosynthesis of carnosine and anserine by reaction with histidine or 1-methyl histidine. Excess purines are metabolized to xanthine (2,6-dihydroxypurine) and finally uric acid (2,6,8-trihydroxypurine).

Uric acid is mainly synthesized in the liver and thereafter released in the circulation. In extracellular fluids (e.g. synovial fluid or blood plasma) it occurs in the ionized form. Normal levels in blood serum are three to 6–7 mg/100 ml. The latter concentration is similar to or above the solubility product of monosodium urate at 37° C., which indicates the risk for (local) precipitation of urate crystals. Urate is normally predominantly (>⅔) cleared via the urine.

Hyperuricemia is defined as that situation when serum urate is bove 7.0 mg/100 ml in men and above 6.0 mg/100 ml in women. The occurrence of hyperuricemia is associated with disorders like obesity, hypertension, alcohol abuse, and congestive heart failure, though it is not considered to be a cause of these disorders. Nevertheless hyperuricemia may lead to diseases like gouty arthritis, uric acid urolithiasis and even nephropathies and also occurs in the syndrome of Lesch-Nyhan. Therefore it is important to ensure that at all times urate levels in serum and urine remain at normal magnitudes.

Uric acid contributes under normal conditions significantly to the total antioxidant (radical scavenging) capacity of blood plasma. It has been reported that total antioxidant capacity can be important for detoxifying reactive species, such as free radicals, e.g. those that are released during uncontrolled inflammatory conditions, and toxic (exogenous) compounds. It is also reported that scavenging of free radicals is important to prevent damage to membranes of cells.

Compounds that are normally used as antioxidants such as ascorbic acid and tocopherols have to be administered in huge amounts in order to have them contribute to the same extent to the total antioxidant capacity of blood plasma. This would lead to undesirable side effects in the product, and, on the longer term, also in persons who consume such a product, due to the pro-oxidant effect of these components. Administration of other redox-active compounds to meet the same antioxidant capacity as urate may lead to undesirable side-effects such as interaction with other circulating antioxidants/radical scavengers such as serum albumin.

Urate is normally produced from xanthine by the enzyme xanthine dehydrogenase. Under certain conditions this enzyme is converted to xanthine oxidase. In this form the enzyme uses oxygen as oxydant and hydrogen peroxide is formed. It is important that the latter compound is neutralized before it can cause harm.

Therefore a need exists to develop a preparation that ensures a constant and sufficiently high antioxidant capacity of extracellular fluids such as blood plasma without undesirable side effects in both product and patients.

Due to their importance for life, nucleotides are rapidly metabolized and a high turnover rate exists. Some metabolites can interconvert using well-described pathways. These pathways are highly regulated and interdependent. Under normal conditions these pathways occur rapidly. This ensures a rather constant concentration of all nucleotides and/or related metabolites, whose magnitude depends on the requirements that are set by the condition of the various tissues and cells and on local concentrations of many components that are involved in TNM.

Under several conditions the human body is not able to maintain homeostasis of all nucleotides and related metabolites in all tissues or cells.

Several diseases have been associated with problems with nucleotide metabolism and in particular ATP levels of specific tissues. In ischaemic situations, tissue concentrations of ATP rapidly decrease and the same occurs in protein-energy malnutrition.

Therefore a need exists for nutritional preparation that ensures the presence of adequate amounts of nucleotides in the different tissues and in such a way that no imbalances occur between the amounts of the various metabolites.

The relevance of the presence of adequate concentrations of various nucleotides has been recognized in the field of infant formula, in particular to ensure development or maintenance of a proper gut function in the young infant. Specific amounts of various nucleotides or their metabolic equivalents are added to obtain a result. See for example WO 95/18618 and WO 95/18547. The composition of human milk is used as reference.

However, the amounts of nucleotides required by the various tissues under varying conditions have not been described in the art. This applies to the developing gut in the premature child, but also to tissue that has been damaged due to trauma, radiotherapy or surgery or for temporary local requirements of tissue that comprises rapidly dividing cells. Also it has not been known up to now how much of a daily oral dose of some milligrams per day is really available to individual patients.

Administration of nucleotide mixtures may thus easily result in either ineffective dosages or overdosages of specific nucleotides or metabolites thereof. Imbalances with regard to the amount or type of nucleotides or related metabolites may also easily disturb normal metabolic processes in cells, especially in sensitive cells like erythrocytes.

In manufacturing practice, it appears that nucleotides are expensive ingredients, which make it difficult to manufacture effective preparations at a reasonable price for the consumer.

For these reasons other components were sought that could be used in nutritional preparations and could influence nucleotide levels.

Glutamine, as important donor of amine groups, plays a role in nucleotide biosynthesis. Kovacevic demonstrated in 1987 that administration of glutamine together with inosine increased cellular ATP content. Administration of glutamine alone was not effective.

EP-A 0 540 462 discloses the use of L-glutamine or its functional equivalents for the treatment of a fall in blood L-glutamine level in people involved in endurance exercise, physical activity or suffering from overtraining.

D-Ribose is a pentose that occurs in many organisms. It is one of the metabolites of glucose when the latter is metabolized in the human body via the oxidative pentose pathway. This pathway yields pentose phosphates that can interconvert and yields glyceraldehyde 3-phosphate, which can be used as energy source.

Ribose can also be activated by ATP to 5-phosphoribosyl-1-pyrophosphate (PRPP), which is involved in the de novo biosynthesis of purines and pyrimidines in a very energy (ATP)-demanding synthetic route and in salvage pathways of these bases.

Nutritional preparations which comprise ribose as single active component are available commercially and are used to increase body performance of sportsman.

WO 99/65476 describes the use per daily dose of 0.1–100 g of a pentose, preferably ribose, and preferably 1–20 g, optionally together with creatine, magnesium, carnitine and arginine to increase energy levels of an organism in vivo. In DE 19659755 Pliml discloses that 1–50 g/day ribose can be used to increase performance for sportsman. The combination of 0.2–2, g/day ribose and 0.1–1 g/day magnesium aspartate was disclosed by Palazzi in WO 92/15311.

Carniglia disclosed in U.S. Pat. No. 5,391,550 that oral administration of a product that comprises ribose, amino acids and a compound selected from the group choline, inositol and carnitine was effective in increasing intracellular ATP levels and for improving wound repair. Preferably the composition comprised 10–40 parts ribose, 30–60 g amino acids and 10–30 parts of either choline, carnitine or inositol or combinations thereof. The latter components are in our opinion not required to support TNM and are therefore not included in the products according to the invention.

U.S. Pat. Nos. 4,719,201 and 4,605,644 disclose the effect of ribose, optionally with adenine for improving recovery after ischaemia, when the compound is present in a solution for perfusing a tissue e.g. during surgery. In U.S. Pat. No. 4,880,783 a heart perfusate is disclosed which comprises adenosine, ribose and hypoxanthine and increases the period of time in which the heart is deprived from a normal oxygen supply during surgery.

None of these papers reveal beneficial effects from ribose other than the increase in intracellular ATP and improvement of wound healing. Also no measures have been disclosed to avoid too large amounts of ribose to be converted to nucleotides and uric acid. Neither a synergy in effect has been reported when folic acid or possibly other active components, is administered together with ribose, especially in those persons that have consumed diet that is improper for their condition.

The prior art discloses that in some cases large amounts of ribose (up to 100 g) must be consumed to observe a beneficial effect. This poses significant problems to the person who suffers from a bad appetite or restrictions in the volume of diet that he/she can consume per day, such as the elderly.

Therefore a need exist for a nutritional preparation that is more effective in supporting total nucleotide metabolism in the body without causing the disadvantages of the prior art. Support of the total nucleotide metabolism should lead to an increase of the levels of all nucleotides and related metabolites in all tissues, especially those in need thereof, but only to optimal values. This should lead to the use as defined in the next clause. Disadvantages associated with the use of prior art products are a high price and a significant risk on metabolic disturbances especially in sensitive cells by administration of higher amounts of specific nucleotides and the risk of hyperuricemia and associated diseases.

SUMMARY OF THE INVENTION

It has been found that a nutritional preparation that comprises ribose, or its functional equivalents, and folic acid, or its functional equivalents, supports total nucleotide metabolism in persons in need thereof. This support is achieved by optimally using the metabolic and regulating systems as present in the body of the mammal. This results in a situation that local shortages in supply of nucleotides or related metabolites are earlier restored and the risk on hyperuricemia is lower than when methods are used as described in the prior art. Ribose should be used in an amount of at least 0.5 g per daily dosage, up to about 40 g per daily dosage. Folic acid (folate) should be used in an amount of at least 100 µg/day, up to about 20 mg/day.

The components are food grade, non-toxic, have a natural origin, are readily available at a specified quality and a reasonable price and are not complicated to include in a wide range of dietetic or nutritional preparations. In addition they have a good taste.

In order to increase the effect of the preparations or to decrease the risk of imbalances in TNM, it is preferred, according to the invention, to include other components as well. The components can be magnesium, orotate, niacin, selenium, thiamin, vitamin B6, glucose, citrate, specific amino acids such as histidine or glutamine, phosphate, sulfate or vitamin B12, their equivalents and/or combinations thereof.

The compositions according to the invention can be used to regulate and support TNM total nucleotide metabolism. It has been found that this effect is advantageous in the prevention and treatment of a wide range of diseases, disorders and health problems. These include trauma, surgery, inflammation (either acute and chronic), subfertility, pregnancy, lactation problems, gut disorders (e.g. mucositis, inflammatory bowel disease, Crohn's disease), infant nutrition (jaundice, gut maturation), cancer, arthritis (osteo-, rheumatoid) and other joint problems, vascular problems and cardio-or cerebro vascular problems, ischaemia (imparted peripheral blood supply, infarcts), aging, respiratory infections, impaired immune function (such as after chemotherapy and during AIDS), burns, sepsis, malnutrition (e.g. protein energy malnutrition, or malnutrition in elderly, cachetic patients and patients suffering from chronic obstructive pulmonary disease or lung emphysema), problems with liver (e.g. cirrose or hepatitis), pancreas or kidneys, malaria, cystic fibrosis, migraine, neurological problems such as Huntington, Parkinson, Alzheimer, schizophrenia and depression, improvement of sports results, muscle soreness, drug intoxication and pain.

The products are preferably fortified with components that are specific for the groups of patients for which the products will be used, as described in detail below.

DETAILED DESCRIPTION OF THE INVENTION

The nutritional, pharmaceutical or dietetic preparation according to the invention can be manufactured in dry form, for example as bar, as powder, as tablet, bar cookie or as cereal. The preparations can also have a liquid form, e.g. as drink, served as ready to drink, as pudding, as sauce as capsule or as (soup) concentrate.

The preparations are manufactured using methods that are known in the art. For example powders can be manufactured by spray-drying or drying on drums. Spray-dried powders can be agglomerated in order to modify bulk density or solubility performance (e.g. wettability). When powders are manufactured, methods for preventing sticking of the powder can be taken that are known in the art, e.g. the addition of specific agents such as tricalcium phosphate or silicon dioxide. When tablets are manufactured the usual tabletting agents (such as magnesium stearate) are included. In order to give the nutritional preparations optimal organoleptic properties, methods can be used that are known in the art, such as setting of pH and the addition of flavoring agents and colorants. Also preservatives can be added to increase shelf life, and whose use is known in the art.

Appropriate amounts of the ingredients are blended in order to manufacture the final product. The final product can also comprise separate compartments that each may comprise part of total number or amount of the ingredients that are required.

The final product can be packaged in a way that is suitable for the type of product that is selected. These ways are known in the art. For example liquids can be packaged in bottles or cartons, that have a volume that is appropriate for containing the volume that is required.for 0.5–10 daily doses. Powders can for example be packed in cans, bags or sachets. These packages can have a volume of typically 0.5–50 daily doses.

The active components can be mixed with other ingredients that are suitable. For example powdered forms of the preparations according to the invention can use spray-dried proteins of dairy, vegetable or animal origin, such as skimmed milk powder, whey powder, egg white powder, potato protein, soy protein, etc. or hydrolysates, or mixtures thereof. It is preferred to use proteins that are relatively rich in histidine and glutamine and poor in tryptophan, such as caseins. Specific synthetic amino acids, such as L-histidine, or peptides, such as alanyl-gluamine or glutamyl-glutamine, may be added to achieve this goal.

When proteins are included in the nutritional preparations, the amount that is included depends on the application of the product. In complete formulae typically an amount of 5–120 g per daily dose is included. In complete formulae for young infants the amount will be in the range 5–15 g per daily dose and preferably 6–10 g per daily dose. In complete enteral nutrition for feeding surgery patients typically 50–120 g and preferably 60–90 g per daily dose are included.

In supplements typically 0–60 g protein per daily dose will be included. In supplements for sportsmen and persons that temporarily have high protein requirements (such as burn patients) or deficiencies in amino acid status (e.g. due to malnutrition) up to 60 g protein per daily dose can be included.

In other situations protein is not included in the product or present in lower amounts, typically 0–20 g per daily dose. In supplements it is advantageous to include free amino acids, especially histidine, in particular the L-isomer. In some cases the support of TNM should be combined with support of growth and anabolism.

It appears that especially a mixture of histidine, the branched chain amino acids leucine and isoleucine, lysine, methionine and phenylalanine has anabolic properties. For example in products for sportsmen the following mixture of amino acids appeared to be especially beneficial for muscle growth, when consumed in an amount of more than 2 and preferably more than 4 g per daily dose: 3–10 wt % histidine, 5–15 wt % isoleucine, 10–23 wt % leucine, 10–23 wt % lysine, 5–15 wt % methionine, 5–15 wt % phenylalanine and 5–15 wt % threonine. The product should in such a case contain no or little protein.

When relative large amounts of proteins or amino acids are included in the product it is preferred to increase the amount of vitamin B6 in the product. The extra amount that should be included in the product can be determined by using the criterium: 2 mg extra vitamin B6 per 100 g protein equivalent. As vitamin B6, source, pyridoxine, pyridoxamine or pyridoxal or functional equivalents thereof can be used.

Also powdered carbohydrates can be used that should be able to serve as glucose provider. Glucose syrup (dried) or starches and especially their hydrolysates are useful. In sweet products it is preferred to use malto-dextrins that are heavily hydrolyzed. In more salty products lightly hydrolyzed maltodextrins should be used, preferably those having a degree of hydrolyses below twelve.

It is important to include glucose into the product, because it allows biosynthesis of sufficient amounts of reducing equivalents and of chemical energy. Both are essential for total nucleotide metabolism. In addition glucose can neutralize excess ribose, which reaction is supported by thiamine phosphate and magnesium. From glucose also extra ribose can be formed in those situations that: (1) too little ribose is administered via the claimed products or (2) too little ribose is present in tissue, relative to the requirements that are put by the specific conditions of the tissue. It is therefore preferred to include in the product 1–50 g glucose or its functional equivalent and more preferably 2–20 g is included.

Also 0.4–10 mg, and preferably 1.0–8 mg thiamin per daily doses, or its functional equivalents should be included. Preferably the hydrochloric acid salt is used.

As source of the active components either pure chemical substances or their functional equivalents such as racemic mixtures or food grade extracts of raw materials or mixtures thereof can be used as ingredients.

D(-)Ribose is a pentose sugar that can be purchased as crystalline product. Ribose is also a main constituent of nucleic acids. These nucleic acids can be isolated from yeast or liver. Either the nucleic acid fraction or extracts of hydrolysates thereof can be used as ribose source. It is preferred to use a preparation that comprises a higher amount of ribose than of the sum of nucleotides, nucleosides and nucleic acid bases, due to the imbalances in endogenous nucleotide concentrations that could occur. It is also possible to use rough extracts from carbohydrate hydrolysates. For example potato starch can be converted by an enzymatic process into a ribose-rich ingredient. Most preferable ribose, when referred to in the specification, does not include nucleic acid bound ribose.

It is preferred to use synthetic ribose, either as racemate, but most preferably as D(-)ribose. When D(-)ribose is used as ribose source per daily dose about 0.5–40 g should be included in particular 1–15 g and most preferably 2–10 g. When other materials are used as ribose source it depends on the ribose content of the ingredient how much of that raw ingredient should be included in the composition.

Where reference is made in this specification to folic acid or folate, all functional equivalents of folic acid are included. Folate is a vitamin that can be purchased as free folic acid (pteroylmonoglutamic acid) or folinic acid (formyl-tetrahydrofolic acid). Also polyglutamate forms can be used as functional ingredient, especially when also zinc is present in the formulation. Rich sources of folate are yeast and liver and extracts of some green vegetables (broccoli, brussels sprouts, spinach) or fruits (citrus fruit) on the condition they are standardized on folate content. It is preferred to use synthetic folic acid. In order to be effective the compositions should comprise at least 100 $\mu$g folate per daily dose. This limit is selected to support adequately total nucleotide metabolism in young infants. In adults the amounts that are required have to be higher: preferably more than 250 $\mu$g have to be supplied per daily dose and most preferably more than 400 $\mu$g. In those adults that suffer from a genetically a compromised enzyme-system to metabolise folate even higher amounts are required, e.g. more than 1 mg/day. For normal adults it is most preferred to include maximally 5 mg folate in the product. When amounts above 4 $\mu$g folic/folate per kg body weight are supplied per day, it is preferred that at least 1 $\mu$g vitamin B12 per 100 mg folate is included.

To observe an optimal effect it is required to include niacin into the product. Niacin appears to have a synergistic effect when supplied together with ribose and folate, with regard to support of TNM and the formation of DNA and RNA. At least 4 mg niacin equivalents (=NE) should be included, in products for adults in particular 30–200 mg NE per daily dose. It is thought that in this dose niacin provides in many persons extra reducing equivalents to diseased tissue to allow increased production of chemical energy and conversion of different forms of nucleotides and of folates and increase formation of DNA and increase tissue levels of triphosphorylated forms of all nucleotides.

It is also preferred to include magnesium in the formulae. It appears that magnesium deficiencies occur rather frequently. Deficiencies will cause a decreased capacity to transfer activated phosphates to other molecules. Magnesium should be present in an amount of at least 20 mg per daily dose. Products for adults comprise preferably per daily dose (dependant on the application of the product) 100–500 mg.

It is important to include several compounds that are able to influence rates of desirable metabolic patterns. For this reason the product should preferably include histidine. Histidine is also added to neutralize excess beta-alanine and permit biosynthesis of sufficient carnoserine and anserine. Typically the amount of histidine will be about 0.2–5.0 g per daily dose and preferably 0.3–3 g per daily dose. Preferably glucose is also present when histidine is present, with a histidine to glucose weight ratio of 0.015 to 1.5. The product should not be fortified with synthetic tryptophan or peptides.

Endogenous inorganic phosphate is an important regulator of pathways. In addition it is important to avoid deficiencies. When phosphate is included in the product, the amount per daily dose will be in the range 20–2000 mg, and preferably 100–1000 mg.

Citrate can be used in the form of pure cristalline citric acid or salts thereof, but also be present in extracts of fruit (oranges, lime). When citrate is included the pH of the final product should be in the range 3–8 and preferably 6–7.5. The amount of citrate per daily dose of product should be 0.1–6 g and preferably 0.3–3 g, dependant on the use of the product.

Orotate is defined as being those components that after consumption will provide orotate ions in the blood plasma.

Suitable sources are orotic acid (6-carboxy-2,4-dihydroxypyrimidine), salts thereof such as sodium or potassium or zinc salts, esters such as choline— or methyl esters and extracts that are rich in orotic acid such as certain extracts from liver. Also precursors like arginine, glutamine or aspartate can be used.

In order to be effective, the product should comprise 0.1–8 g orotate per daily dose. This amount is in general less than the amount of ribose or glutamine in the product and should be determined by using the criterium that about 0.04–0.3 g orotate is given per kg body weight. When arginine or aspartate is used as precursor for orotate, per day more than 1 g should be administered and preferably more than 5 grams. Orotate is claimed to ensure proper biosynthesis of pyrimidines and to neutralise excess of ribose that may get formed in the specific conditions of that patient. This also would ensure sufficient tissue levels of beta-alanine, carnosine and anserine.

It is found that inclusion of vitamin B12 in the product increases nucleotide levels in tissue. As source of vitamin B12, cobalamines, such as cyanocobalamine can be used. The quantity should be 0.2–4000 µg and preferably 0.5–5 µg per daily doses.

As mentioned above it is important to include vitamin B6 when the product is meant to be used for the prevention or treatment of some cerebral disorders or neurodegenerative diseases such as Parkinson, Huntington, Alzheimer, ADHD, depression, schizophrenia and mood disorders. This amount should be 2–10 mg and preferably 2–4 mg per daily dose. For other applications, such as infant formula, the product can comprise less vitamin B6. In general the preparations according to the invention will comprise 0.3–10 and preferably 0.5–4 mg per daily dose.

Selenium is preferably included into the product to ensure a proper supply of this key component for the enzyme catalase. As selenium source selenium salts such as sodium selenite can be used but also extracts of raw materials that are rich in selenium such as selenium yeast. The amount to be included is 10–300 µg and in particular for products for adults 40–150 µg per daily doses.

Other food grade components such as lipids (in general), additional vitamins, minerals, trace elements, carnitine, creatine, coenzyme Q10, conjugated linoleic acid (CLA), alpha-lipoic acid or their functional analogues or fibre could be part of the composition, dependant on the application of the nutritional compositions. The use of these components for disease-specific nutritional compositions is disclosed in the prior art.

Long-chain polyunsaturated fatty acids, especially ω-3 unsaturated fatty acids such as DHA, EPA and stearidonic acid are preferably included in compositions intended for suppressing the immune function of patients. These fatty acids may originate from known sources such as marine algal oils, fish oils, selected vegetable oils (e.g. from Echium) or from synthetic sources.

The invention also pertains to a method of enhancing uric acid antioxidant capacity in blood plasma, comprising administering an effective amount of at least one compound selected from ribose and folate. The effective amounts depend on the condition of the subject and on the required antioxidant power, and can be selected from those given in table 1. Other antioxidants may also be present, although preferably at lower doses than commonly used.

Clinical Use

Conditions for which the compositions of the invention can be used include in general those conditions in which the biosynthetic capacity is insufficient, e.g. due to metabolic disorders or nutrient deficiencies. In such conditions large amounts of specific nucleotides and/or related metabolites are required locally, e.g. due to diseases or local disorders or specific demands, and transport of nutrients and TNM components is imparted.

Persons that would benefit from these products are persons that have a general insufficiency to synthesize, salvage or convert nucleotides such as those suffering from protein-energy malnutrition and persons that suffer from an inherited disturbance in the expression of one of the enzymes that are involved in TNM. The same general problem can occur in premature or young infants due to an underdevelopment of their enzyme systems. Also many elderly persons and persons suffering from liver problems (for example due to alcohol abuse or hepatitis) have insufficient capacity for nucleotide synthesis due to imparted enzyme systems and need support of the most critical steps in TNM.

The product is also meant to be used in those conditions that locally and sometimes temporarily very high requirements exist for nucleotides or related metabolites and the requirements cannot readily be met by available biochemical capacity. In case of trauma (for example after an accident or surgery) locally high amounts of all nucleotides must be generated in order to repair (replace) damaged tissue. During various inflammatory disorders during some stages lymphocytes rapidly proliferate, which puts high demands on nucleotide supply to synthesizing tissues. In addition it is beneficial to increase total antioxidant capacity of the relevant extracellular fluids, especially in those situations that an uncontrolled inflammatory reaction exists.

High amounts of nucleotides must also be available locally during spermatogenesis, during lactation and in bone marrow during periods of (increased) synthesis of blood components. The product is therefore also claimed to be useful for improving subfertility, increasing milk quantity and quality of milk during lactation and useful when used after surgery. Nutritional products according for these types of patients may be fortified with trace elements, minerals and vitamins to meet their nutritional requirements. Products for use after surgery should preferably comprise a protein and lipid source isolated from egg or milk and growth factors, such as insulin-like growth factors and epidermal growth factors.

Under normal conditions gut epithelial cells have a relatively short half-life and are produced from specialized stem cells. During proliferation but also during maturation (migration) nucleotide and/or energy requirements of these cells are high. Several gut disorders are associated with a very high throughput of gut epithelial cells, which requires local availability of large amounts of various nucleotides. Inclusion of glutamine or its equivalents will further enhance the effectivity of the nutritional compositions of the invention, especially when administered at more than 1 g per daily dosage.

Also during recovery after chemo- or radiotherapy, large amounts of nucleotides must be available in the right relative proportions. During therapy large numbers of cells will die due to apoptosis and large amounts of nucleotides are released. Once these have been metabolized extra biosynthetic capacity is required, to meet the high demands. The nutritional compositions of the invention will support recovery after damage due to chemotherapy especially in the mucosal tissue.

Temporary insufficiencies in biosynthetic capacity of nucleotides become in particular evident during ischaemic situations as may occur during trauma, surgery and cardioand cerebrovascular problems. The decreased blood supply causes that low amounts of nucleotides or related metabolites are offered to the underlying tissues. It is thought that by supplying the claimed product, the concentrations of the required nucleotides or related products are sufficiently higher to improve the status of tissue that suffers from a bad blood supply. In case the tissue is brain tissue, the product will decrease the amount of excitatory amino acids, such as glutamate, that will be released.

Also during and after heavy exercise, existing deficiencies in tissue nucleotide content and/or imparted capacity for TNM become evident. Pools of ATP will rapidly become depleted and it will take a relatively long time before tissue that has been damaged during exercise will be repaired or replaced. This will lead to muscle soreness and injuries. The product is also claimed to be useful in treatment of MS and fatigue.

Nucleotides play an important regulating role in cell metabolism, and can serve as donor or acceptor of amine groups in catabolism of aspartate in periods that demands on muscle are high and blood supply does not meet requirements.

The product is further claimed to be useful in the prevention of cancer. Without wanting to be bound by theory it is thought that adenine and PRPP are involved in the polymerization of ADP-ribose onto nuclear proteins, which are important for cell regulation and DNA repair. Improvement of the possibilities for repair of damaged DNA then prevents the development of tumor cells.

The product is further claimed to be especially useful in the prevention and treatment of rheumatoid arthritis and other joint problems. It is thought that the product operates by means of its effect on sulphation capacity. This would lead to an increase in concentrations and/or variety of sulphated polysaccharides in interstitial and synovial fluid, thus improving the lubricating properties.

It is also claimed that the products improve immune function. Without wanting to be bound by theory, we think that this effect is thought to the effect of the formulations on mucus composition and levels of endogenous amounts of glycoproteins, immunoglobulins and proteoglycans. These components are essential for proper functioning of membrane structures including their recognition function and the functioning of enzymes, in particular with regard to their specificity. This beneficial effect on the barrier function of mucus is claimed to be particularly relevant for persons suffering from respiratory infections or common cold.

The preparations are further claimed to be useful in preventing problems with blood supply to tissues. This is thought to be due to the improvement of blood clotting parameters and the effect on microvascularisation. The products are further helpful in the treatment of cystic fibroses and treatment or prevention of malaria and tuberculose. The effect of the product is further enhanced by fortification with vitamin B6, especially in an mount of more than 3 mg/day.

The product is further claimed to be useful in the treatment of intoxications, e.g. due to drug abuse but also due to problems with bilirubine metabolism. It is thought that the product ensures sufficient glucuronidation or sulphation conjugation. The product also supports regulation of steroid metabolism.

The product is also claimed to be useful in the treatment of pain as may become evident in attacks of migraine and pain on the chest after an infarct. It is thought that the product regulates the amount of adenosine in such a way that the vasodilatation effect is maintained and local sudden rises in concentration are avoided.

The product is also claimed to be helpful in treating patients suffering from or at risk for developing renal failure, ischaemic events such as infarcts and cerebrovascular accidents, inflammatory bowel disease and cancer. This is thought to occur via restoration of tissue levels of beta-alanine, carnosine and anserine.

In case the product is used in the treatment or prevention of cardio or cerebro vascular problems it is useful to include creatine, carnitine, coenzyme Q10, taurine, vit B12, vit B6, Zn and/or Mg in the product.

The product is also claimed to be beneficial in the treatment of disorders associated with imbalances in neurotransmitter levels in the brain. Imbalances in neurotransmitter levels in the brain occur in persons that suffer from Parkinson's disease, Alzheimer's disease, ADHD, schizophrenia, depression and mood disorders. The effect is thought to get obtained via an increase in effectivity of vitamin B6, either co-administered or already present in the body, and a regulation of metabolism of dopamine, adrenaline, serotonin and noradrenaline.

TABLE 1

List of the active components of the nutritional preparation:

| Ingredient/component | Amount per daily dose | | |
|---|---|---|---|
| | full range | preferred range | most preferred range |
| Ribose | 0.5–40 | 1–15 | 2–10 g |
| Folate | >100 | 250 µg–20 mg | 400 µg–5 mg |
| Niacin | | >4 | 30–200 niacin equivalents |
| Magnesium | | >20 | 100–500 mg |
| Glucose | | 1–50 | 2–20 g |
| Protein | | 0–120 g | |
| Histidine | | 0.2–5 | 0.3–3 g |
| Inorganic phosphate | | 20–2000 | 100–1000 mg |
| Vitamin B1 | | 0.4–10 | 1–8 mg |
| Vitamin B12 | | 0.2–4000 | 0.5–5 µg |
| Glutamine | | 0.5–30 | 1–10 g |
| Orotate | | 0.1–8 g | |
| Citrate | | 0.1–6 | 0.3–3 g |
| Selenium | | 10–300 | 40–150 µg |
| Vitamin B6 | | 0.3–10 | 0.5–4 mg |

EXAMPLES

1. Nutritional preparation for improving exercise performance of sportsman

Ingredients per daily dose:

3 g of an amino acid mixture that consists of 10 wt % histidine, 10 wt % isoleucine, 20 wt % leucine, 15 wt % lysine, 12 wt % methionine, 10 wt % phenylalanine and 13 wt % threonine 5 g D-ribose 10 g maltodextrins DH 19

2 g MCT oil

200 µg Folic acid 30 mg Niacin 0.5 g orotic acid 500 mg magnesium phosphate 50 mg α-lipoic acid The product is packed in a sachet for reconstitution in a glass of water, fruit juice or milk, or similar liquid.

2. Powdered nutritional supplement that contains per daily dose:

17 g of an amino acid mixture that consists of 2 g glutamine, 0.7 g arginine, 0.5 g histidine, 0.4 g isoleucine, 1.0 g leucine, 0.9 g lysine, 0.3 g methionine, 0.3 g phenylalanine, 0.3 g threonine, 0.6 g valine.
6 g D(−)ribose
20 g maltodextrin
300 µg folic acid
40 mg niacin
2 mg thiamin.HCl
2 µg cyanocobalamine
1.0 g sodium orotate
400 mg alpha-lipoic acid
225 µg biotin
15 mg pantothenic acid
1 mg pyridoxine.HCl
0.5 g potassium carbonate
0.5 g sodium citrate
0.5 g sodium chloride
0.6 g magnesium chloride
0.6 g tri-calcium phosphate
50 mg ascorbic acid
20 mg α-tocopherol
Trace of flavouring agent Eight daily doses of are packed in a 500 g can.

3. Dietetic preparation for gastrointestinal problems (IBD, M. Crohn, sepsis, food allergy)

Oral rehydration drink that contains per liter
5 g yeast extract
3 g D(−)ribose
5 g maltodextrins DH 10
600 µg folic acid
5 µg cyanocobalamine
20 mg zinc sulfate
4 mg Cu chloride
300 mg magnesium phosphate
1 g orotic acid
5 g glutamyl-glutamaat
160 µg sodium selenite 3. Pharmaceutical preparation for pregnant or lactating women Cup having a volume of 200 ml that comprises a pudding based on skimmed milk powder that comprises per 200 ml:
3 g D-ribose
400 µg folic acid
4 µg cyanocobalamine
4 mg pyridoxamine
100 mg magnesium chloride
25 mg zinc citrate
0.4 g methionine
10 g maltodextrin
1 g pectin 4. Supplement for persons suffering from vascular problems (cardiovascular, atheroscleroses, cerbrovascular diseases, infarcts, decreased blood supply to legs, bad vessel quality) Bar (weight about 28 g ingredients, including moisture) that comprises:
15 g glucose syrup
4 g D-ribose
400 µg folic acid
3 ug cyanocobalamine
30 mg zinc sulfate
250 mg magnesium carbonate
3 mg pyridoxamine
2 g arginine.HCl
2 g dried fruit (apple, pear and apricot)
2 g grain flocks (rye, wheat, oats)
5 g mixture of nut pieces (hazlenut)
1 g creatine
30 mg alpha tocopherol
50 mg ascorbic acid
20 mg coenzyme Q10

5. Product to support liver function in case of liver cirrhoses, alcohol abuse, hepatitis, etc.
5 g Yeast extract
3 g D(−)ribose
2 g glutamine
10 g maltodextrins DH 19
400 µg folic acid
4 ug cyanocobalamine
3 mg pyridoxine
1 g arginine
2 g sodium ate
1 g aspartate
2 mg thiamin.HCl
40 mg zinc carbonate
4 mg copper carbonate
150 µg potassium selenate 6. Soup for the elderly
A dried soup concentrate is prepared from
5 g Powdered broccoli extract, providing 180 µg folate
5 g Powdered yeast extract, providing 100 ug folate and 3 g ribose
200 ug folic acid
1 g D(−) ribose
3 µg cyanocobalamine
0.5 g sodium chloride
0.4 g potassium chloride
1 g dried carrot pieces
1 g dried onion pieces
20 mg zinc sulfate
2 g maltodextrin 7. Complete formula for prematures to reduce risk of jaundice Infant formula for reducing risk of jaundice comprising per 100 g powder:
12.4 g protein equivalents in the form of whey/casein 60/40 w/w
54.8 g digestable carbohydrates of which 2 g D(−) ribose
21.1 g lipids
5 g fibre
standard quantities of trace elements, minerals and vitamins as known in the art except that 110 ug folic acid is included 8. Supplement for improving immune function
Cookie for improving immune function
A wheat-based cookie comprising per 30 g
2 g glutamine
3 g ribose
10 g maltodextrine that includes 200 ug docosahexaenoic acid, 200 ug Eicosapentaenoic acid and 100 ug arachidonic acid
  20 mg zinc
  100 mg magnesium
  400 ug folic acid
  3 ug vitamin B12
  4 mg copper
  0.3 g citric acid
9. Powder for prevention and treatment of osteoarthritis, comprising per 40 g
  300 ug folic acid
  4 g D(-) ribose
  0.5 g methionine
  2 ug cyanocobalamine
  0.8 g sodium citrate
  0.5 g histidine
  4 mg pyridoxine.HCl
  14 mg zinc
  200 mg magnesium
  200 mg sulphate
  9 g casein
  20 g maltodextrines
  4 g soy lecithin

We claim:

1. A method of improving total nucleotide metabolism, comprising administering to a subject in need thereof, effective amounts of ribose and folate, the ribose being administered as free ribose, ribose containing nucleic acid, hydrolysate of ribose containing nucleic acid, ribose containing carhoydrate, hydrolysates of ribose containing carbohydrate or a combination thereof.

2. The method of claim 1, said effective amounts being 0.5 g–40 g of ribose per daily dosage, and 100 μg–20 mg of folate, per daily dosage.

3. The method of claim 2, said effective amounts being 1 g–20 g of ribose per daily dosage, and 100 μg–20 mg of folate, per daily dosage.

4. The method of claim 3, said effective amounts being 1 g–15 g of free ribose per daily dosage, and 250 μg–5 mg of folate, per daily dosage.

5. The method of claim 1, further comprising administering at least one component selected from the group consisting of magnesium, orotate, niacin, selenium, thiamin, glucose, citrate, histidine, phosphate, sulfate and vitamin B12.

6. The method of claim 5, comprising administering 0.2–3.0 g of histidine or its nutritional equivalent.

7. The method of claim 5, comprising administering more than 0.3 g of histidine, per daily dosage or per 5 g of ribose.

8. The method of claim 5, comprising administering 4–200 mg niacin equivalents, per daily dosage or per 5 g of ribose.

9. The method of claim 5, comprising administering 0.1–8 g orotate, per daily dosage or per 5 g of ribose.

10. The method of claim 5, comprising administering 1–50 g glucose, per daily dosage or per 5 g of ribose.

11. The method of claim 1, further comprising administering 5–120 g of protein, per daily dosage or per 5 g of ribose.

12. The method of claim 1, further comprising administering more than 0.5 g of glutamine, and/or more than 1 g of aspartate and/or more than 1 g or arginine, per daily dosage or per 5 g of ribose.

13. The method of claim 1, further comprising administering more than 2 g, per daily dose, of a mixture of amino acids or amino acid equivalents containing 3–10 wt % histidine, 5–15 wt % isoleucine, 10–23 wt % leucine, 10–23 wt % lysine, 5–15 wt % methionine, 5–15 wt % phenylalanine and 5–15 wt % threonine.

14. The method of claim 1, further comprising administering histidine, glutamine, asparatate and/or arginine, wherein at least 50% of the histidine, glutamine, aspartate and/or arginine is in the form of free amino acids or dipeptides.

15. The method of claim 1, comprising administering glucose and ribose in a weight ratio of glucose to ribose of 0.1–50.

16. The method of claim 15, in which the weight ratio of glucose to ribose is 0.2–10.

17. The method of claim 1, wherein said subject suffers from a condition selected from trauma, surgery, inflammation, subfertility, lactation problems, gut disorders, cancer, arthritis and other joint problems, vascular problems, cardio- or cerebrovacular problems, ischaemia, impaired immune function, burns, sepsis, malnutrition, problems with liver, pancreas or kidneys, malaria, cystic fibrosis, tuberculosis, fatigue, MS, migrane, neurological problems, Huntington, Parkinson, Alzheimer, schizophrenia, depression, respiratory infections, muscle soreness, drug intoxication and pain.

18. The method of claim 1, wherein said subject is in need of improvement of immune functions, said method further comprising administering Ω3 polyunsaturated fatty acids at a level of more than 500 mg per daily dose.

19. The method of claim 1, wherein said subject is in need of improvement of immune functions, said method further comprising administering glutamine at a level of 1–10 g per daily dosage.

20. The method of claim 1, wherein said subject suffers from malaria or neurologic disorders, said method further comprising administering vitamin B6 at a level of 0.3–10 mg per daily dosage.

21. The method of claim 1, wherein said subject is susceptible to or suffers from cardiovascular or cerebrovascular disorders, said method further comprising administering at least one member of the group, carnitine, creatine, coenzyme Q10, taurine, betaine, alpha-lipoic acid, vitamin B6, vitamin B12, zinc and magnesium.

22. The method of claim 1, wherein said subject is in need of improving the barrier function of mucus.

23. The method of claim 1, wherein said subject suffers from cystic fibrosis, malaria or tuberculosis.

24. The method of claim 1, wherein said subject is in need of supporting the regulation of steroid metabolism.

25. A method of enhancing uric acid antioxidant capacity in blood plasma, comprising administering an effective amount of at least one compound selected from ribose and folate, the ribose being administered as free ribose, ribose containing nucleic acid, hydrolysate of ribose containing nucleic acid, ribose containing carbohydrate, hydrolysate of ribose containing carbohydrate or a combination thereof.

26. The method of claim 25, said effective amount being 1 g–20 g of ribose per daily dosage, and/or 250 μg–2.0 mg of folate, per daily dosage.

27. The method of claim 1, wherein said subject is selected from infants and athletes.

28. The method of claim 1, wherein said subject is pregnant.

* * * * *